United States Patent
Shaw

(10) Patent No.: US 7,366,719 B2
(45) Date of Patent: Apr. 29, 2008

(54) METHOD FOR THE MANIPULATION, STORAGE, MODELING, VISUALIZATION AND QUANTIFICATION OF DATASETS

(75) Inventor: Sandy C. Shaw, San Francisco, CA (US)

(73) Assignee: Health Discovery Corporation, Savannah, GA (US)

( * ) Notice: Subject to any disclaimer, the term of this patent is extended or adjusted under 35 U.S.C. 154(b) by 0 days.

(21) Appl. No.: 10/959,844

(22) Filed: Oct. 6, 2004

(65) Prior Publication Data

US 2005/0076190 A1   Apr. 7, 2005

Related U.S. Application Data

(63) Continuation-in-part of application No. 10/887,624, filed on Jul. 10, 2004, which is a continuation-in-part of application No. 09/766,247, filed on Jan. 19, 2001, now Pat. No. 6,920,451.

(60) Provisional application No. 60/486,233, filed on Jul. 10, 2003, provisional application No. 60/177,544, filed on Jan. 21, 2000.

(51) Int. Cl.
*G06F 7/00* (2006.01)
*G06F 9/30* (2006.01)

(52) U.S. Cl. ............ 707/6; 707/1; 707/7; 707/10; 709/1; 709/206; 712/217

(58) Field of Classification Search ............ 707/6, 707/7, 100–104.1
See application file for complete search history.

(56) References Cited

U.S. PATENT DOCUMENTS

| | | | |
|---|---|---|---|
| 4,210,961 A | 7/1980 | Whitlow | |
| 5,416,848 A * | 5/1995 | Young | 382/191 |
| 5,490,061 A * | 2/1996 | Tolin et al. | 704/2 |
| 5,577,249 A | 11/1996 | Califano | |
| 5,706,498 A | 1/1998 | Fujimiya | |
| 5,717,788 A | 2/1998 | Barnsley | |
| 5,802,525 A | 9/1998 | Rigoutsos | |

(Continued)

OTHER PUBLICATIONS

Peter Tino, "Spatial Representation of Symbolic Sequences through Iterative Function Systems" IEEE Transactions on Systems, vol. 29, No. 4, Jul. 1999, pp. 386-393.*

(Continued)

*Primary Examiner*—Cam-Y Truong
*Assistant Examiner*—Anh Ly
(74) *Attorney, Agent, or Firm*—Procopio, Cory, Hargreaves & Savitch, LLP; Eleanor M. Musick

(57) ABSTRACT

There is described a method for manipulation, storage, modeling, visualization, and quantification of datasets, which correspond to target strings. An iterative algorithm is used to generate comparison strings corresponding to some set of points that can serve as the domain of an iterative function. The comparison string is scored by evaluating a function having the comparison string and one of the plurality of target strings as inputs. The score measures a relationship between a comparison string and a target string. The evaluation may be repeated for a number of the other target strings. The score or some other property corresponding to the comparison string is used to determine the target string's placement on a map. The target string may also be marked by a point on a visual display.

11 Claims, 8 Drawing Sheets

U.S. PATENT DOCUMENTS

| | | | |
|---|---|---|---|
| 5,838,832 A | 11/1998 | Barnsley | |
| 5,857,036 A | 1/1999 | Barnsley | |
| 5,884,016 A | 3/1999 | Allen | |
| 5,893,095 A | 4/1999 | Jain | |
| 5,960,430 A * | 9/1999 | Haimowitz et al. | 707/6 |
| 5,960,437 A * | 9/1999 | Krawchuk et al. | 707/102 |
| 5,977,890 A * | 11/1999 | Rigoutsos et al. | 707/101 |
| 6,018,735 A * | 1/2000 | Hunter | 707/5 |
| 6,083,693 A * | 7/2000 | Nandabalan et al. | 435/6 |
| 6,092,065 A * | 7/2000 | Floratos et al. | 707/6 |
| 6,104,989 A * | 8/2000 | Kanevsky et al. | 707/2 |
| 6,108,666 A * | 8/2000 | Floratos et al. | 707/104.1 |
| 6,141,657 A * | 10/2000 | Rothberg et al. | 707/6 |
| 6,223,186 B1 | 4/2001 | Rigault | |
| 6,243,713 B1 | 6/2001 | Nelson | |
| 6,333,092 B1 * | 12/2001 | Gipple et al. | 428/172 |
| 6,334,132 B1 * | 12/2001 | Weeks | 707/101 |
| 6,366,280 B1 | 4/2002 | Allen | |
| 6,373,971 B1 * | 4/2002 | Floratos et al. | 382/129 |
| 6,389,428 B1 * | 5/2002 | Rigault et al. | 707/104.1 |
| 6,453,246 B1 | 9/2002 | Agrafiotis | |
| 6,507,843 B1 | 1/2003 | Dong | |
| 6,603,472 B2 | 8/2003 | Allen | |
| 6,663,803 B1 * | 12/2003 | Gipple et al. | 264/40.1 |
| 6,850,252 B1 * | 2/2005 | Hoffberg | 715/716 |
| 6,920,451 B2 * | 7/2005 | Shaw | 707/6 |
| 2001/0037999 A1 * | 11/2001 | Martin | 219/121.85 |
| 2001/0047376 A1 * | 11/2001 | Shaw | 709/1 |
| 2003/0130797 A1 * | 7/2003 | Skolnick et al. | 702/19 |
| 2003/0151556 A1 * | 8/2003 | Cohen | 343/700 MS |
| 2003/0182246 A1 * | 9/2003 | Johnson et al. | 705/76 |
| 2005/0026199 A1 * | 2/2005 | Shaw | 435/6 |
| 2005/0079524 A1 * | 4/2005 | Shaw | 435/6 |
| 2005/0158736 A1 * | 7/2005 | Shaw | 435/6 |
| 2006/0013473 A1 * | 1/2006 | Woodfill et al. | 382/154 |
| 2006/0200253 A1 * | 9/2006 | Hoffberg et al. | 700/19 |

OTHER PUBLICATIONS

Yukio Tominaga & Iwao Fujiwara, "Data Structure Comparison using Fractal Analysys", Elservier Science B. V. vol. 39, No. 2, Dec. 19997, pp. 187-193.*

Christos Faloutsos & King-Ip Lin: "FastMap: A fast Algorithm for Indexing, data-Mining and Visualization of traditional and Multimedia Datasets" International Conference on Managament of Data, proceedings of 1995 ACM SIGMOD, 1995, pp. 163-174.*

Daniel P. Fasulo, Tao Jiang, Richard M. Karp, Reuben Settergren and Edward C. Thayer "An Algorithmic Approach to Multiple Complete Digest Mapping", Computational molecular Biology-Jan. 1997, ACM-1997 (pp. 118-127).

Shaw et al., "A Novel Method For Visualizing Similarity In gene Expression And Other Large Datasets," Proceedings of the ISCA 16th International Conference, Mar. 28-30, 2001.

Tino, P., "Spatial Representation of Symvolic Sequences Through Iterative Function Systems," IEEE Transactions on Systems, Man and Cybernetics—Part A: Systems and Humans, vol. 29, No. 4, Jul. 1999, pp. 386-393, XP002166332.

Tominaga Y., et al., "Data structure comparison using fractal analysis," Chemometrics and Intelligent Laboratory Systems, NL, Elsevier Science Publishers, B.V. Amsterdam, vol. 39, No. 2, Dec. 1, 1997, pp. 187-193, XP004108621.

* cited by examiner

METHOD FOR THE MANIPULATION, STORAGE, MODELING, VISUALIZATION AND QUANTIFICATION OF DATASETS

CROSS-REFERENCE TO RELATED APPLICATIONS

This application is a continuation-in-part of U.S. application Ser. No. 10/887,624, filed Jul. 10, 2004, which claims priority to Provisional Application Ser. No. 60/486,233, filed Jul. 10, 2003 which is incorporated herein in its entirety and made a part hereof. This application is also a continuation-in-part of U.S. patent application Ser. No. 09/766,247, filed Jan. 19, 2001, which claims priority to Provisional Application Ser. No. 60/177,544 filed Jan. 21, 2000 which are incorporated herein in their entirety and made a part hereof.

FEDERALLY SPONSORED RESEARCH OR DEVELOPMENT

Not Applicable.

BACKGROUND OF THE INVENTION

1. Technical Field

This present invention relates to methods of manipulation, storage, modeling, visualization and quantification of datasets.

2. Background Art

The standard techniques currently employed to analyze large datasets are Cluster Analysis and Self-Organizing Maps. These approaches can be effective in identifying broad groupings of genes connected with well understood phenotypes but fall short in identifying more complex gene interactions and phenotypes, which are less well defined. They do not allow for the fingerprinting and visualization of an entire dataset, and missing values are not easily accommodated. The computational requirements are high for these techniques, and the mapping time increases exponentially with the size of the dataset. Furthermore, the current data must be reanalyzed when new datasets are added to the analysis, and vastly different results can occur for each new dataset or group of datasets added.

In order to take full advantage of the information in multiple, large sets of data, we need new, innovative tools. There is a need for methods that more easily enable identification and visualization of potentially significant similarities and differences between multiple datasets in their entirety. There is also a need for methods to intelligently store and model large datasets.

Recent studies have revealed genome-wide gene expression patterns in relation to many diseases, and physiological processes. These patterns indicate a complex network interaction involving many genes, and gene pathways, over varying periods of times. On a parallel track, recent studies involving mathematical models and biophysical analysis have shown evidence of an efficient, robust, network structure for information transmission when these networks are examined as large-scale gene groups. The problem comes in producing analysis of information transmission and network structure on the scale of individual genes and genetic pathways. Fractal Genomics Modeling (FGM) solves this problem by taking advantage of universal principles of organization. From the Internet, to social relations, to biochemical pathways, the fundamental patterns are similar. The natural relationship among many different types of networks, when mathematically represented, enables the extrapolation of vast quantities of data, capable of computerized analysis. FGM is computationally efficient because the method is performed incrementally, is almost perfectly parallel, and is substantially linear. Consequently, there is no scaling problem with FGM. Furthermore, of significant interest, FGM can be used to identify biomarkers and develop systems for diagnoses or prognoses of disease by exploiting the map of interactions and causality-pathway conjecture-rendered by this technology.

BRIEF DESCRIPTION OF THE DRAWINGS:

These and other aspects and attributes of the present invention will be discussed with reference to the following drawings and accompanying specification.

DETAILED DESCRIPTION OF THE INVENTION

The present invention is susceptible to embodiments in many different forms. Preferred embodiments of the invention are disclosed with the understanding that the present disclosure is to be considered as exemplifications of the principles of the invention and are not intended to limit the broad aspects of the invention to the embodiments illustrated.

Generation of Point-Models of Datasets in a Multi-Dimensional Map

Figure 1A:
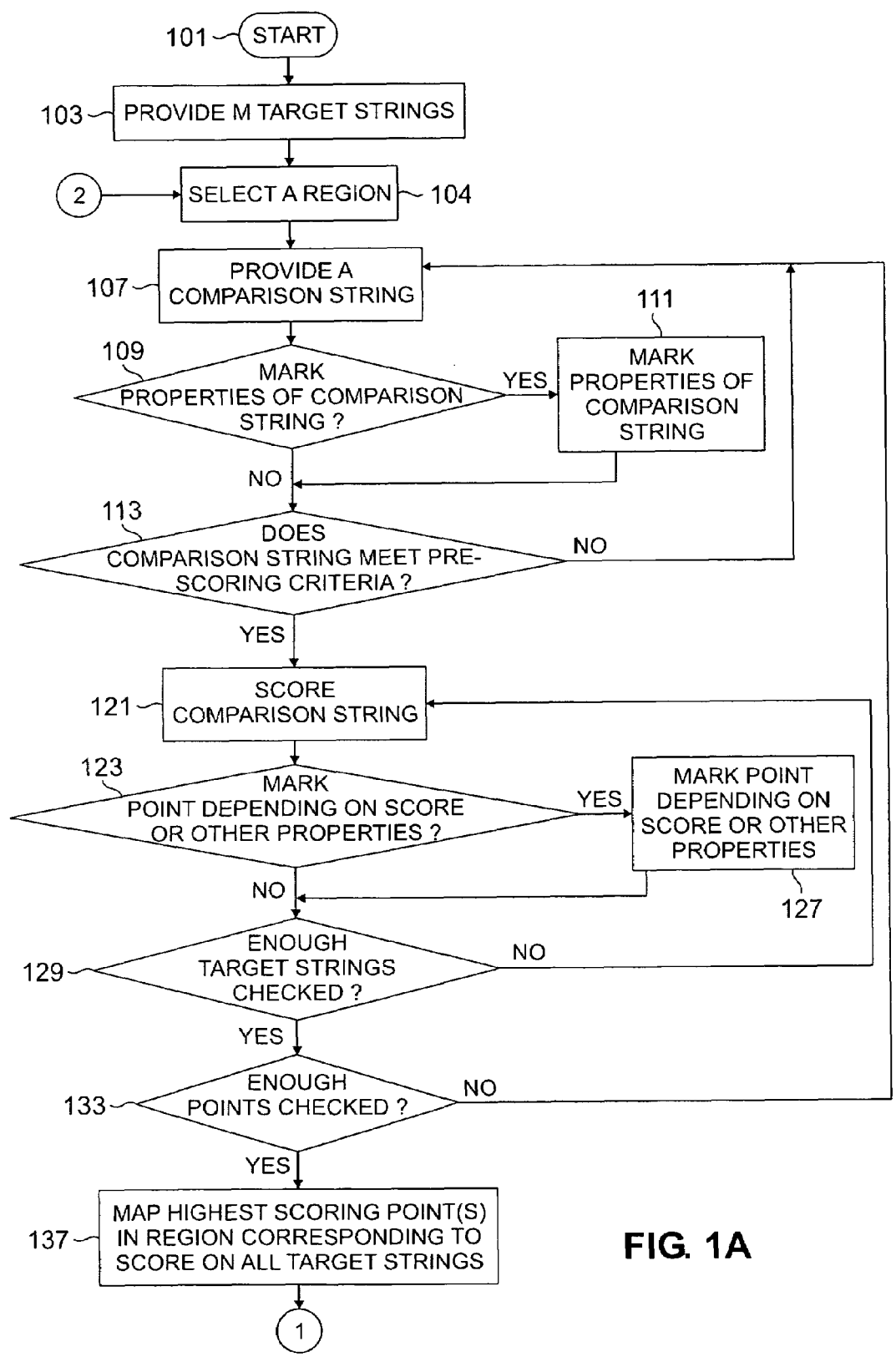
FIGS. 1A and 1B are a flow chart of the operational steps for manipulation, storage, modeling, visualization and quantification of datasets.
Figure 1B:
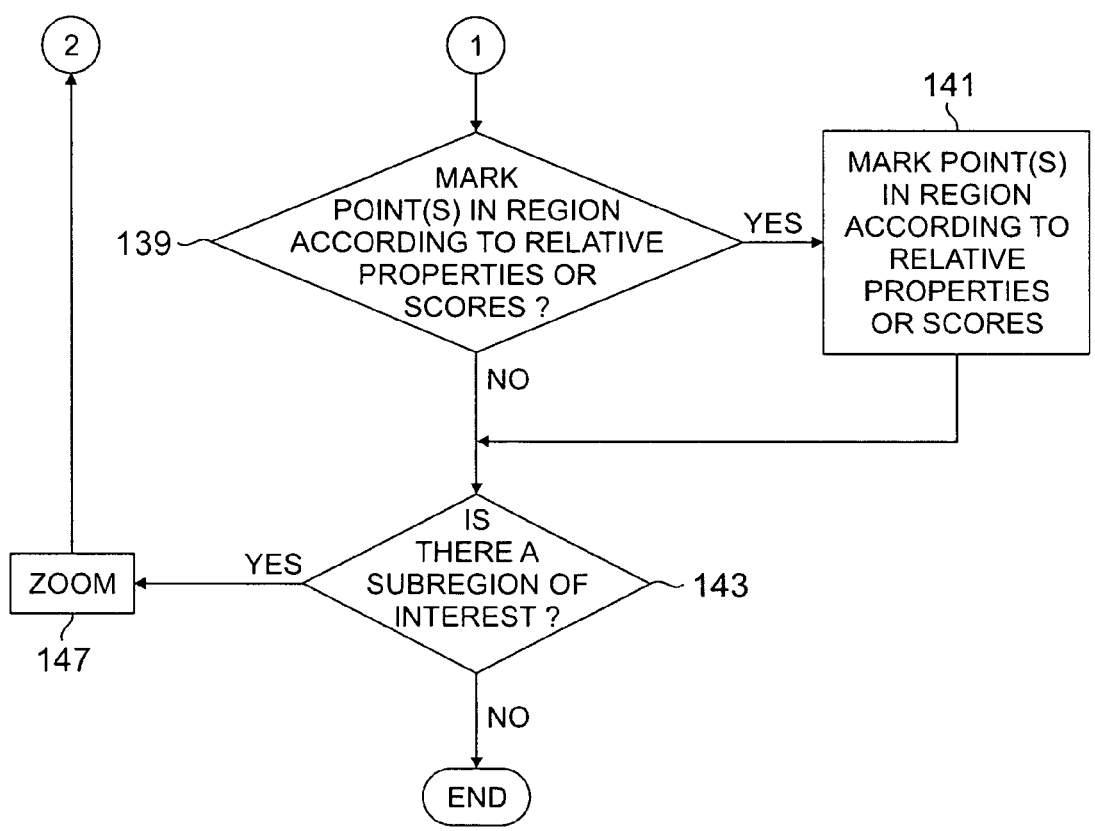

This present invention relates to methods of manipulation, storage, modeling, visualization and quantification of datasets. FIGS. 1A and 1B show a flow chart of the method of the present invention for generating a multi-dimensional map of one or more target strings in which the target strings can be represented by marked points in the map. The target strings correspond to datasets to be analyzed. Each point marked in the map serves as a point-model for one or more target strings. The method can be used in the manipulation, storage, modeling, visualization and quantification of datasets in the target strings. The dataset in each target string consists of a sequence of numbers of length N*. One example of a dataset to be analyzed and its corresponding target string is the yearly income of a population, the target string being each person's income listed in a sequence. Another example is the body temperature readings of a group of patients in a hospital ward, with the target string being those readings listed in a sequence. A further example is a DNA sequence, such that each different type of base (A, C, T, G) is labeled with a number (0, 1, 2, 3), producing a target string with a corresponding numerical sequence. A further example is a protein sequence, such that each type of amino acid in the protein chain is labeled with a different number, producing a target string with a corresponding numerical sequence.

For FIGS. 1A and 1B, suppose each dataset to be analyzed is a string of measurements resulting from an experiment involving several thousand genes. Further suppose that there is a number connected with the experimental result from each gene. Such a number could be the gene expression ratio, which represents the differences in fluorescence calculated from the gene combined with some other chemical on a biochip or on a slide. This calculation is not a part of the present invention but provides the numbers in the example target strings. The number of numbers in the example target strings is N*.

Starting with FIG. 1A, the method starts (step 101) by providing a set of M such target strings of length N* (step 103). A region, R, is selected (step 104) such that each point in the region can serve as the domain of an iterative function. The iterative algorithm calculates the comparison string from a point, p, in some region, R. Preferably, the region, R, is in the complex plane corresponding to the area in and around the Mandelbrot Set. Although the Mandelbrot Set is used in the preferred embodiment of the present invention, other sets, such as Julia Sets, may also be used. Using this iterative method, every point within the Mandelbrot Set can be made to correspond to a data sequence of arbitrary length. Because the Mandelbrot Set is made up of an infinite number of points, the method allows any number of datasets containing any number of values to be compared by mapping the datasets to points in or near the Mandelbrot Set.

The Mandelbrot Set is an extremely complex fractal. The term fractal is used to describe non-regular geometric shapes that have the same degree of non-regularity on all scales. It is this property of a self-similarity that allows pictures of artificial systems built from fractals to resemble complex natural systems.

Figure 2:
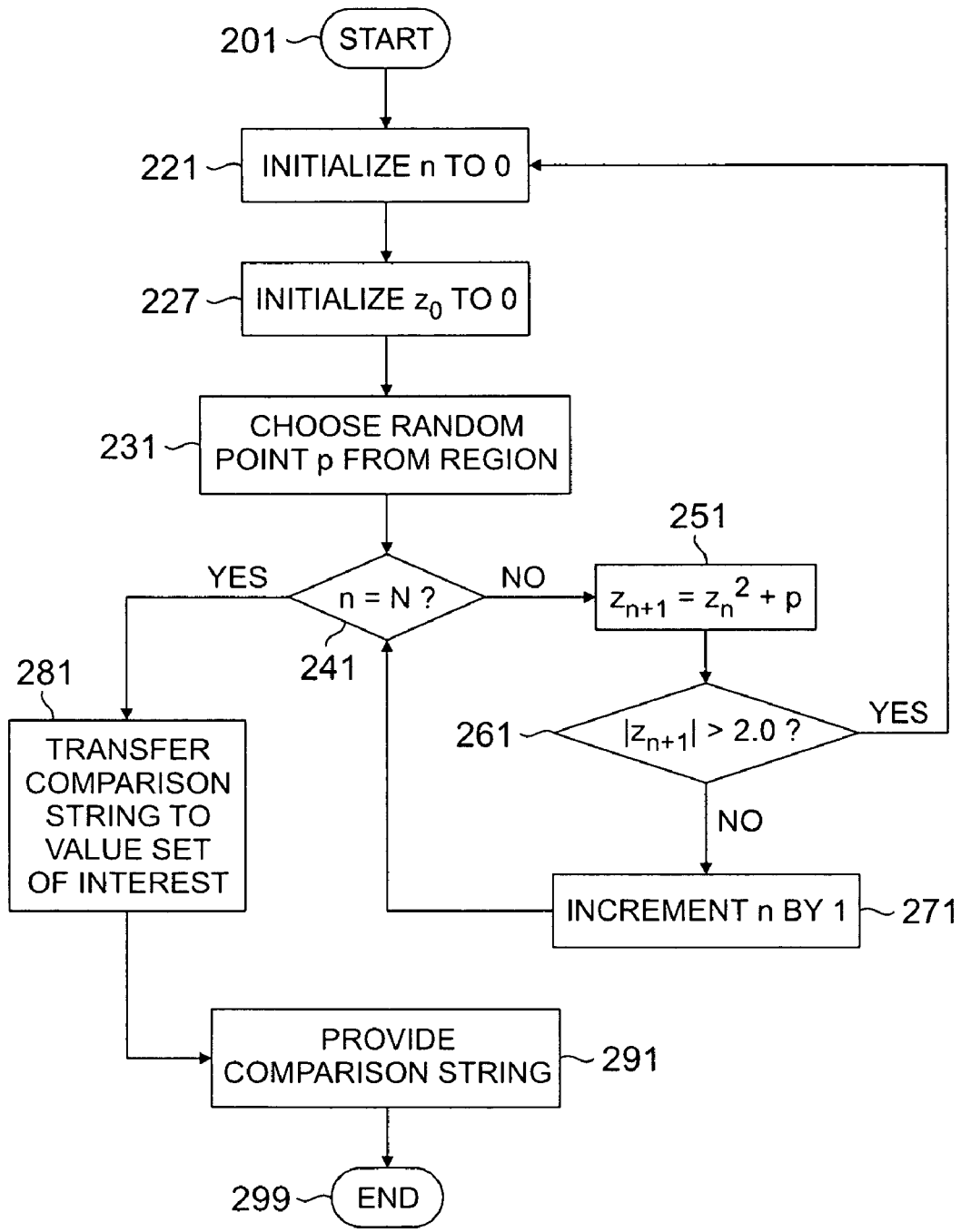
FIG. 2 is a flow chart of the operational steps for an iterative algorithm and processing which provides a comparison string.

A comparison string of length N is also provided (step 107). The comparison string is generated from a point, p, in the Region, R, by using an iterative algorithm N times to generate the comparison string having a length of N. The comparison string is also a data string and may be of any length relative to the target string. FIG. 2 shows an example of the steps involved in an iterative algorithm to generate a comparison string of length N provided in step 107 of FIG. 1A. The algorithm of FIG. 2 for the Mandelbrot Set is an example of an algorithm that can be used. If a set of points from a different iterative domain is used in this method instead of the Mandelbrot Set, a different algorithmic function would instead be used for that different set of points. The algorithm starts (201), and a counter, n, is initialized to zero (step 221). A variable to be used in the algorithm, $z_0$, is initialized to zero (step 227). A point p is chosen from region R, preferably the region corresponding to the area in and around the Mandelbrot Set (step 231). An example of choosing such a point might be to overlay a grid upon the Mandelbrot Set and, then, choose one of the points in the grid.

Determine if N numbers, which constitute the comparison string, have been calculated (step 241). In other words, check if n=N. If all the numbers of the comparison string have not yet been calculated (step 241), then the point p is used as input to the iterative algorithm $z_{n+1}=z_n^2+p$ (step 251). For example, the first iteration based on a point p is $z_1=z_0^2+p$, or $z_1=0+p$, or $z_1=p$. Since p is a complex number of the form a+bi when decomposed into its real and imaginary parts, $z_2$ takes the form $z_2=(a^2+2i*a*b-b^2)+a+bi$ or $(a^2-b^2+a)+i(b*(2a+1))$.

If the absolute value of $z_{n+1}$ is greater than 2.0, or $|z_{n+1}|>2.0$ (step 261), the iteration is stopped because it is unbounded, and the $z_{n+1}$ will become infinitely large. Thus, point p is no longer under consideration. Instead, n is initialized to zero (step 221), $z_0$ is initialized to zero (step 227), and another point is instead chosen from the region R (step 231), preferably in and/or near the Mandelbrot Set. This prematurely stopped string, however, may be used as a comparison string with a length of less than N.

If the absolute value of $z_{n+1}$ is equal to 2.0 or less, increment n by one (step 271) and check if N numbers have been calculated which constitute the comparison string (step 241). In other words, the algorithm iterates until n=N. If n<N, then perform the next iteration on point p (step 251). This next iteration will calculate the next number in the string of numbers comprising the comparison string. The process iterates until a string of variables, $z_1$ through $z_N$ can be produced that is of length N, so long as $|z_{n+1}|\leq2.0$.

If n=N (step 241), or when the iteration is stopped because the absolute value of $z_{n+1}$ is greater than 2.0, or $|z_{n+1}|>2.0$ (step 261), then the comparison string has been generated. However, the numbers in the comparison string may need to be transformed to have values within a value set of interest (step 281). Suppose the numbers in the example target string representing gene expression ratios are real numbers between 0 and 10. If we wish to explore the similarities between the comparison string and the target string the value set of interest would be the real numbers between 0 and 10. The numbers of the comparison string may need to undergo some transformation to produce real numbers in this range. One way to produce such a real number is the function $r=10.0*b/|z_n|$. This will produce real numbers r falling in the range between 0 and 10 for $z_n$=a+bi. Provide the comparison string (step 291), and the algorithm ends (step 299).

Referring to FIG. 1A, an optional step is to determine if certain properties of the comparison string should be marked (step 109). Examples of properties that might be marked are the mean value of the comparison string or the Shannon entropy. If certain properties of the comparison string should be marked (step 109), mark the properties of the comparison string (step 111). Optionally, the comparison string can also be checked to determine if it meets pre-scoring criteria (step 113), regardless of whether the properties of the comparison string are marked. This step involves preliminary testing of the comparison string's properties alone as criteria to initiate scoring. Examples of pre-scoring criteria are measuring the mean value of the comparison string to see if it is higher or lower than desired and determining if the Shannon entropy of the comparison string is too low or too high. When marking prior to scoring, it may be determined that an entire subregion of the region has a large number of points that do not meet the pre-scoring criteria. For example, this subregion may be part of a grid. It may be determined that the rest of the points in that subregion will not be considered, even though the original intent was to consider all points in the region.

If the comparison string is pre-scored as described above and it does not meet the pre-scoring criteria (step 113), then the current comparison string is no longer under consideration. Another comparison string is instead provided (step 107). The new comparison string is generated using the exemplary iterative algorithm of FIG. 2 on a new point p from region R.

If the comparison string is pre-scored and it meets the pre-scoring criteria (step 113), then scoring of the comparison string is performed (step 121). Scoring refers to some test of the comparison string using the target string. Scoring of the comparison string can also be performed without marking the properties of the comparison string or pre-scoring the comparison string. In the example of real numbers r falling in the range between 0 and 10 described above, the score could be the correlation coefficient between the comparison string consisting of numbers r and the target string. A simple example of scoring might be counting the number of one-to-one matches between the comparison string and the target string over some length L where $L <= N^*$, where $N^*$ is the length of the target string. Alternatively, a one-to-one comparison between numbers in the comparison and target strings may be performed for a non-contiguous number L of the numbers. For example, compare the second, fourth, and sixteenth numbers for a number L=3.

Determine if the point, p, corresponding to the comparison string should be marked depending on the score or other properties (step 123). If it is determined that the point should be marked (step 123), mark the point, p, in the region, R (step 127). The marked point is a point-model in the region, R, to represent the target string, M. The comparison string generated from this marked point with the iterative algorithm represents the target string, M. Marking can be used in an environment where a pixel or character corresponds to point p on a visual display or marking can refer to annotating the coordinates of point p in some memory, a database or a table. The point is marked by changing some graphical property of the corresponding pixel, such as color, or changing the corresponding character. The point may also be marked by annotating the coordinates of point p in some memory, a database or a table based on the score. Optionally, point p can be marked, either additionally or solely, according to quantification of properties of the comparison string, without regard to the score. Such properties can be general, such as using some color, or annotation, to reflect the mean value of the string being in a certain range, or markings reflecting the number of 3's in the string, or the value of the Shannon entropy. Such marking can be used as an aid in searching for preliminary criteria for scoring. When marking point p, it may be determined that an entire subregion of the region has a large number of points that do not meet the scoring criteria or other properties. For example, this subregion may be part of a grid. It may be determined that the rest of the points in that subregion will not be considered, even though the original intent was to consider all points in the region.

If it is determined that the point should not be marked (step 123), determine if a sufficient number of the M target strings have been checked for the comparison string derived from point p (step 129). For instance, in our gene expression example, there may be several experiments or datasets that are being scored against each comparison string. If more of the M target strings should be checked, the comparison string is scored against another of the M target strings (step 121). The comparison string can be used to compare to all M target strings. Not all of the target strings may exhibit similarity to a comparison string, and, therefore, not all target strings may be marked. Also, more than one target string may demonstrate some homology with a comparison string. Moreover, target strings may be marked multiple times, exhibiting correlative relationships to multiple comparison strings.

If a sufficient number or all of the M target strings have been checked (step 129), determine if a sufficient number of points corresponding to comparison strings have been checked (step 133). If more of the points corresponding to comparison strings should be checked, provide another comparison string (step 107). The new comparison string is generated using the same iterative algorithm as used in generating the previous comparison string, such as the one detailed illustratively in FIG. 2, on a new point p from region R. Any number of the same M target strings will then be used to score the new comparison string.

If a sufficient number of points corresponding to comparison strings have been checked (step 133), the scoring process stops. In the case of determining the points, p, from a grid, this could be the number of points in the grid. The highest scoring point or points are then mapped (step 137). Mapping refers to placing the coordinates of highest scoring point or points in memory, a database or a table. The target string or strings may also be visually marked on a visual display.

Target strings may be analyzed and/or compared by examining, either visually or mathematically, their relative locations and/or absolute locations within the region R. When scoring similarity measures between the comparison strings and the target strings, target strings with greater similarity are generally mapped closer to each other based on Euclidean distance on the map. This is because comparison strings with greater similarity are generally closer to each other on the map. However, this is not always true because the metrics involved are more complicated. For example, shading of points corresponding to comparison strings with high scores for a given target string represents a metric which shows similarity between this target string and others mapped in this shaded region. The target strings in this case, however, may not appear close together on the map or display but can be identified as being similar.

Continuing to FIG. 1B, determine whether points in region R should be marked (in a similar manner as previously described) based on their relative scores or properties compared to other points in region R (step 139). If it is determined that the points should be marked (step 139), mark the points (step 141). For example, one might wish to mark all the points whose score falls within 10% of the highest score of a chosen target string, or mark points whose comparison strings have the lowest or highest Shannon entropy for the region. When marking points, it may be determined that an entire subregion of the region has a large number of points that do not meet the relative score criteria or other properties. For example, this subregion may be part of a grid. This may be used to determine whether this subregion is of interest or not.

In one embodiment of the present invention, once the decision has been made as to whether such points should be marked (step 139), determine if a subregion of R is of interest (step 143). If a subregion of R is of interest (step 143), then this subregion is examined with higher resolution, called zooming (step 147). The subregion of R replaces the previous region R. (step 104 of FIG. 1A). Comparison strings will be generated from the new subregion of R and will be scored against any number of the same set of M target strings originally provided. Points in a subregion of interest, which were previously unchecked, will be examined because the new region, R, is a higher resolution version of the subregion of interest. The points in the subregion will tend to produce a greater percentage of similar comparison strings to those previously examined in region R. If the subregion of interest is a high scoring region this will, in general, produce a greater percentage of high scores and some differences will emerge to produce higher scores or properties which are closer to some desired criteria.

After zooming (step 147) and before examining the subregion, the target strings and comparison strings may optionally be transformed to attempt to improve the precision and resolution of the mapping and marking in the method. Suppose in the gene expression example, the target strings values, instead of real numbers from 0 to 10, were binned into 10 contiguous intervals, such that the first bin corresponds to real number values from 0 to 1, the second bin to real number values from 1 to 2, etc. Suppose these bins were labeled 0 to 9. The target string would then be a string of integers with values from 0 through 9. Suppose that a similar transformation was done on the transformed comparison strings. Suppose the method is performed and after zooming (step 147), the gene expression ratios and comparison strings are split into 20 such bins from 0 to 0.5, 0.5 to 1.0, etc. Thus, the target and comparison strings will be re-scaled before repeating the process in the new subregion (104 of FIG. 1A).

This re-scaling can improve the precision and accuracy of the mapping and marking in the method. There are several well studied methodologies that can be used to approach such a re-scaling to improve the precision and resolution of the mapping and marking process as zooming is performed. These include, but are not limited to, methodologies such as Simulated Annealing, Hill Climbing Algorithms, Genetic Algorithms, or Evolutionary Programming Methods.

If no other subregions of R are of interest (step 143), the method of FIGS. 1A and 1B ends (step 199). This generally results when there is no improvement in the score after some number of zooms.

It should be apparent to one skilled in the art that this technique can be used to study the behavior of any (scoring) function that uses the target strings and the comparison strings as variables. Attempting to find the highest value of the similarity measure scoring function is a particular case of this. As such, this method could be used to attempt to optimize any scoring function, using a target string or multiple target strings and comparison strings as variables, to find the functions minima and maxima. In addition, each comparison string can simply be used alone as input into the variables of a scoring function for such a purpose.

It should be apparent to one skilled in the art that this method can be used for data compression. If the model of the target string represented by a comparison string is sufficiently similar to the target string, and the coordinates of the point p corresponding to that comparison string can be represented in a more compact way than the target string, then the target string can be replaced with its more compact representation in the form of the coordinates of point p. This is because the comparison string generation algorithm can then be used to recreate a sufficiently similar representation of target string from point p.

This method has special applicability to multiple large datasets. Uses for this method include analysis of DNA sequence data, protein sequence data, and gene expression datasets. The method can also be used with demographic data, statistical data, and clinical (patient) data. The uses for this method are not limited to these datasets, however, and may be applied to any type of data or heterogeneous mixtures of different data types within datasets. Some of the steps of this method can involve determinations and interventions made by a user of the method or they can be automated.

Fractal Genomics Modeling (FGM)

The previously described method can be adapted for use in a new data analysis technique, Fractal Genomics Modeling (FGM), to explore the structure of genetic networks. It is possible to produce hypotheses for unknown gene interactions, for proposed pathways, and for pathway interconnections of large-scale gene expression through Fractal Genomics Modeling (FGM). By virtue of its correlational power, FGM inherently results in the discovery of putative biomarkers that can classify disease. Such disease indicators are discovered by the rendering and ordering of the underlying genetic elements that engender the illness, as it progresses and changes over time. Three distinct disease models ensue, each exemplifying the predictive capability of FGM: Down's Syndrome, Human Immunodeficiency Virus (HIV) infection, and leukemia.

The conventional approach to analyze of large-scale gene expression has been cluster analysis and self-organizing maps. This approach can be effective in identifying broad groupings of genes connected with well understood phenotypes, but falls short in identifying more complex gene interactions and phenotypes which are less well defined.

When applying cluster analysis to microarrays, typically a function is applied to every gene expression value in such a way that similar values cluster in similar locations on (usually) a two dimensional surface. With FGM, every point on a surface uses its own function to represent a cluster model of gene expression values, effectively "clustering the clusters." This allows for much greater insight into gene expression patterns and the similarities between them. By using FGM, the analysis moves from conventional approaches of examining gene expression values to examining gene expression patterns.

Figure 3:
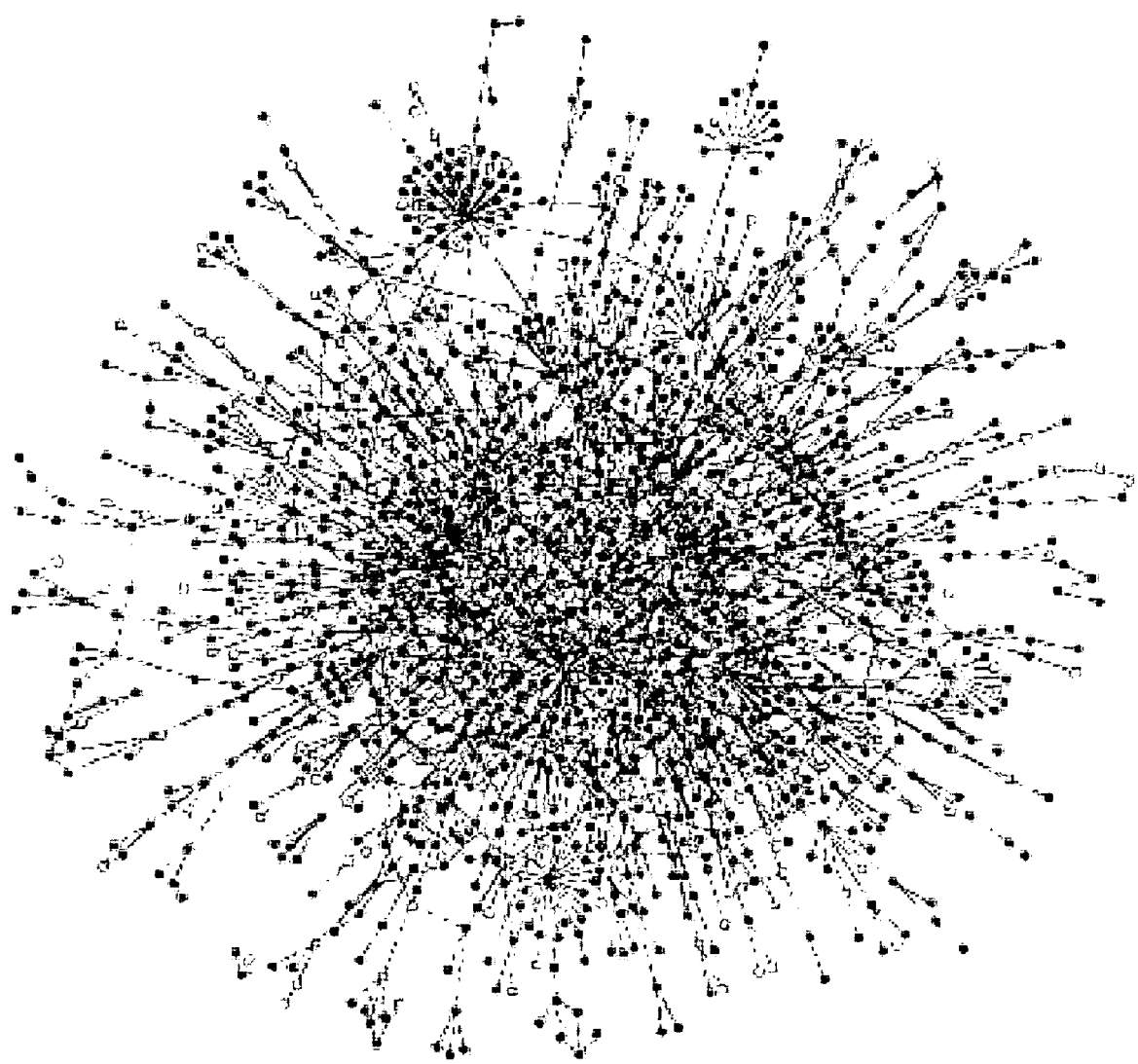
FIG. 3 is a model showing an efficient, robust, network structure for information transmission of the kind that has been found in many complex networks, including gene regulatory networks.

FIG. 3 illustrates an efficient, robust, network structure for information transmission of the kind that has been found in many complex networks, including gene regulatory networks. The points represent what are called nodes in the networks, and the lines represent what are called links. The nature of the type of network shown in FIG. 3 is that there are few nodes with many direct links, forming hubs, and many nodes with only a small number of direct links. These types of networks are often called scale-free or power-law networks. They are characterized by the fact that the number of genes with a given number of links falls off as a power law. For example, there may be twice as many nodes with 2 links as with 4 links. The robust nature of this type of network comes from the fact that if one removes or disables one of the nodes, it is more likely to be one with only a few links and cause less harm to the network as a whole.

Suppose the World Wide Web is organized this way. The points around the center would be web sites like Yahoo or Google, the points slightly further from the center might be web sites like Amazon.com or Expedia, and the outside points might be personal web sites (obviously this requires a much larger picture to show this accurately!). The flow of information tends to go from the inside out. For example, information flows easily from Yahoo to the rest of the network because it has so many direct links. Information flow from a personal web site to the rest of the web is possible, but less likely. One can see the robust nature of the web in the fact that sites and servers go offline all the time without effecting the network. Of course the occasional times when an "inner" site such a Yahoo goes offline can have a very large impact!

Each node in FIG. 3 can also represent a gene and the lines can represent correlated behavior to other genes in a genetic network. The most "connected" genes, or genes with the most direct links, would be ones in the center of this picture.

Figure 4:
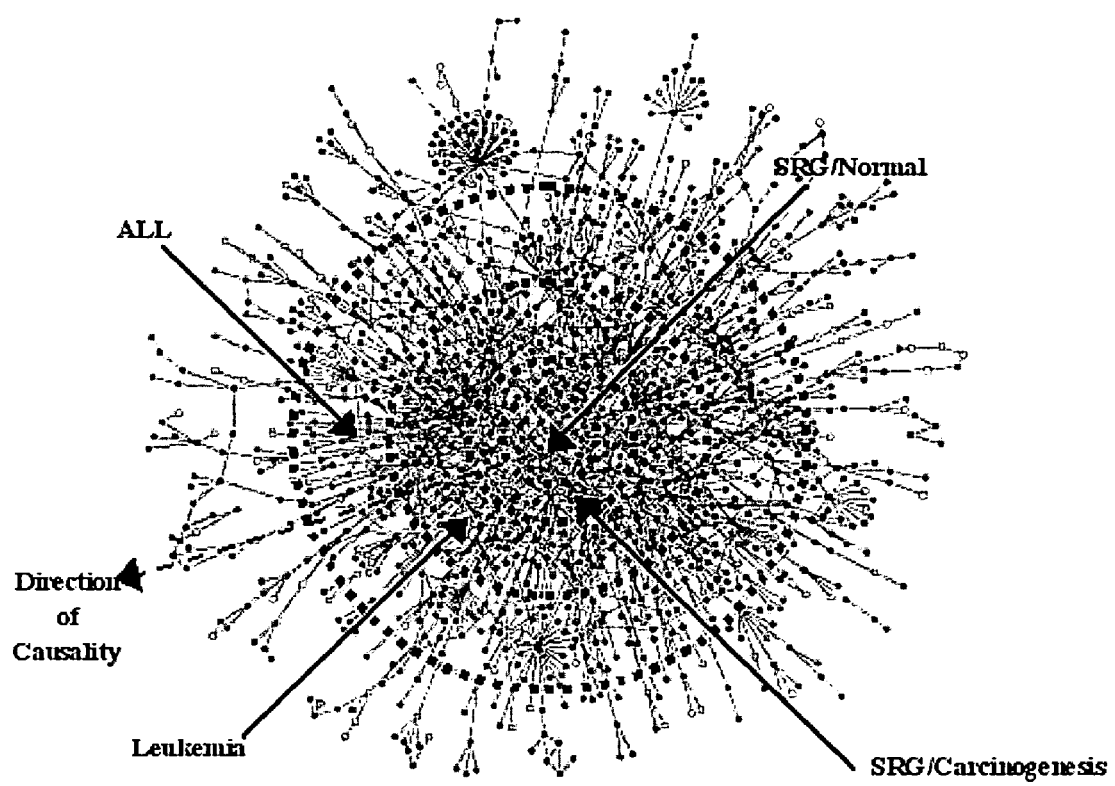
FIG. 4 is a model showing clinical expression of acute lymphoblastic leukemia (ALL) based on gene expression patterns in the ALL genetic network.

As an example, FIG. 4 represents how acute lymphoblasitc leukemia (ALL) might express itself in the genetic network of an actual patient. In this model, the flow of information, in this case biochemical interactions, begins far upstream, in what could be called "super-regulatory genes" (SRG) due to their importance. This area is labeled SRG/Normal. In this patient and in most people, these SRG behave as they would in a normal, healthy individual.

As the biochemical gene expression patterns propagate out of the center through downstream links, however, something occurs which causes a divergence from a normal, healthy pattern. Due to mutation, biochemical or environmental factors, or chance, a group of genes residing somewhere in the ringed area labeled SRG/Carcinogenic begins a cascade through the network that propagates into a clinical expression of cancer. Further downstream are nodes in the network that define the clinical outcome as a specific type of cancer, illustrated by the group of genes labeled Leukemia and, still further downstream, as a subclass of leukemia, ALL (and extending out to genes not seen). It should be noted that this is not a simple cascade from the center outward. Many interconnecting pathways are involved with both promoter and inhibitory links between genes.

FGM is a hybrid technique that blends some of the concepts of wavelet analysis with cluster analysis. FGM "wavelets" are a series of real-valued numbers derived from complex logistic maps, such as Julia sets, generated from iterations of a single point in the complex plane.

FGM searches points on the complex plane for the model that gives the greatest Pearson correlation with the actual localized data, using a minimum cutoff correlation whose absolute value is >0.95. The similarity metric between point-models on the complex plane found in this way is very intricate but, in general, similar models tend to cluster in similar areas on the surface. This is particularly true if the point-models fall within a given "threshold" determined by Euclidean measure.

Since a genome-wide pattern is mirrored in a small number of genes due to underlying fractal structure, FGM can be used to model the gene expression of small groups of genes, each having n number of genes (for example, n is 7 or 14 genes) from a much larger gene pool. The larger gene pool can be a sample of an organism's genome or of an organism's entire genome, such as the entire human genome. Illustratively, the genes in the gene pool can be arranged randomly in microarrays of commercial gene chips (e.g., Affymetrix Human Genome U95A chips consisting of about 12,000 genes) to measure the gene expression levels of the genes. Significantly, at least one small characterizing group of genes must exist.

Since FGM models are usually scored based on their Pearson correlation, the overall magnitude of gene expression within these small groups does not matter in probing for similar patterns throughout the array, only the relative expression patterns within the groups. Other mathematical relations may be used other than Pearson's correlation. When comparing patterns of gene expression between these groups, we sometimes worked with only the models of these gene groups (in "model" space) and sometimes with the actual gene expression values. Unless noted, we usually compare model values and not actual gene expression values although they are often similar.

Choosing gene expression values from small groups of arbitrarily chosen genes in a network is the same as a series of short, random walks of random step-size on such a structure. By analogy, one should see a comparative distribution of gene expression values between such "walks" much different than if genes were randomly linked within the genome or acting largely independently. Similarities between the gene expression patterns in these groups should reveal information about the genetic network structure with correlations between gene groups skewed around gene groups chosen that align with the inherent modularity. Clusters on the FGM surface can serve to identify and to analyze such a skewed distribution.

Identifying Biomarkers

Within the point-models on the FGM surface, clusters are found containing models of the same gene groups corresponding to only one of the phenotypes. If such a gene group is found, it is then individually tested across all datasets to verify that between these n-gene patterns the Pearson correlation is markedly different depending on the phenotype from which the dataset is drawn. If such a gene group is found, further testing is done to choose the n-gene group from the sample within the cluster that produces the most marked difference. Such a gene group and pattern then becomes a candidate biomarker for the particular phenotype being studied and provides insight into the biochemical pathways linked to the phenotype present.

EXAMPLES

Example 1

Evidence of Scale-Free Genetic Network and Identification Biomarkers in Down's Syndrome This example demonstrates the use of FGM both to provide evidence of scale-free genetic network in Down's Syndrome and to identify specific small gene groupings, consisting of 7 genes, that can serve as biomarkers relating to Down's Syndrome.

In this study, FGM was used to model small groups of 7 genes from much larger microarrays (Affymetrix Human Genome U95A chips) consisting of 12,558 genes. The data was derived from fibroblasts of 4 subjects with and 4 subjects without Down's Syndrome—totaling 8 subjects. The number of genes within the groups, in this case 7, was decided using the criteria of picking a relatively small number—in the range of 5-20—that when divided into 12,558 yields a real number without a remainder. Thus, arbitrarily choosing the gene groups by grouping the genes as they appeared on the gene chip, 1,794 7-gene groups were established. Consequently, 14,352 (1,794 gene groups×8 subjects) target strings, M, each with 7 gene expression values, were provided for FGM analysis.

Comparison strings were generated from points in the multi-dimensional map or complex plane for each target string and were scored against each of the target string. These comparison strings served as potential FGM models for the target strings. These FGM models were scored based on their overall Pearson correlation, using a minimum cutoff correlation of absolute value>0.95. Within the point-models on the FGM surface, clusters were found containing models of the same gene groups corresponding to only one of the phenotypes.

In order to test a genetic network for the threshold requirements of scale-free and modular behavior, a log-log plot of k vs. P(k) of gene expression data from a Control/Normal sample and a Down's Syndrome subject is graphed. P(k) is the probability of finding a 7-gene group with k links to another 7-gene group. A group is considered linked to another group if it falls within the same FGM cluster of a given size.

Figure 5:
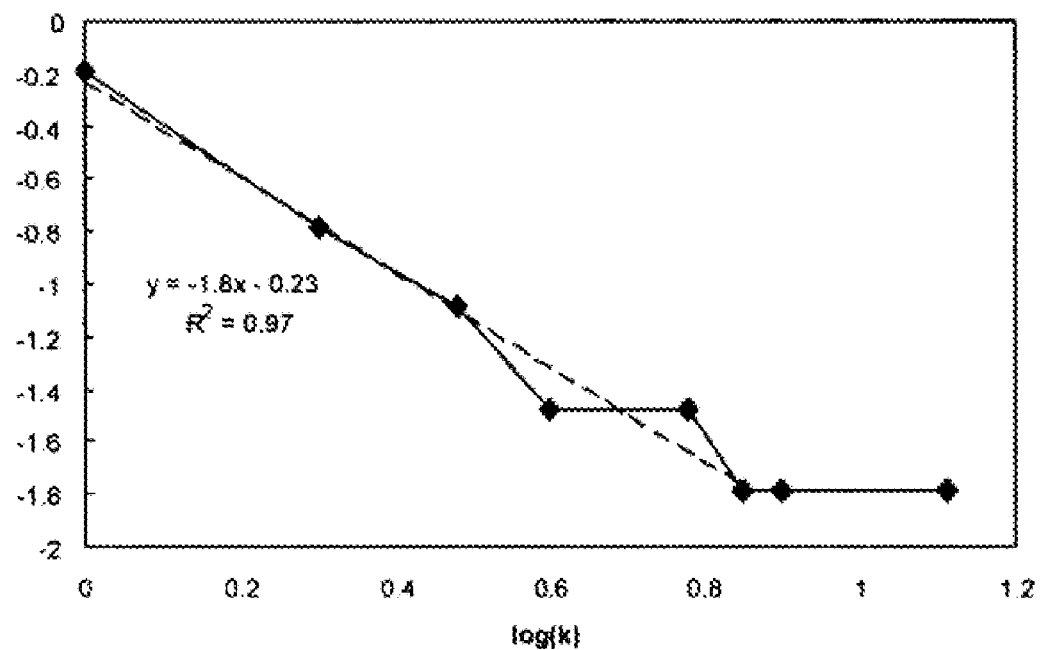
FIG. 5 is a log-log probability distribution for lined FGM models derived from an arbitrarily chosen gene expression data from a sample of Control/Normal subject and Down's Syndrome subject. Dashed line=scale-free fit.
Figure 5:
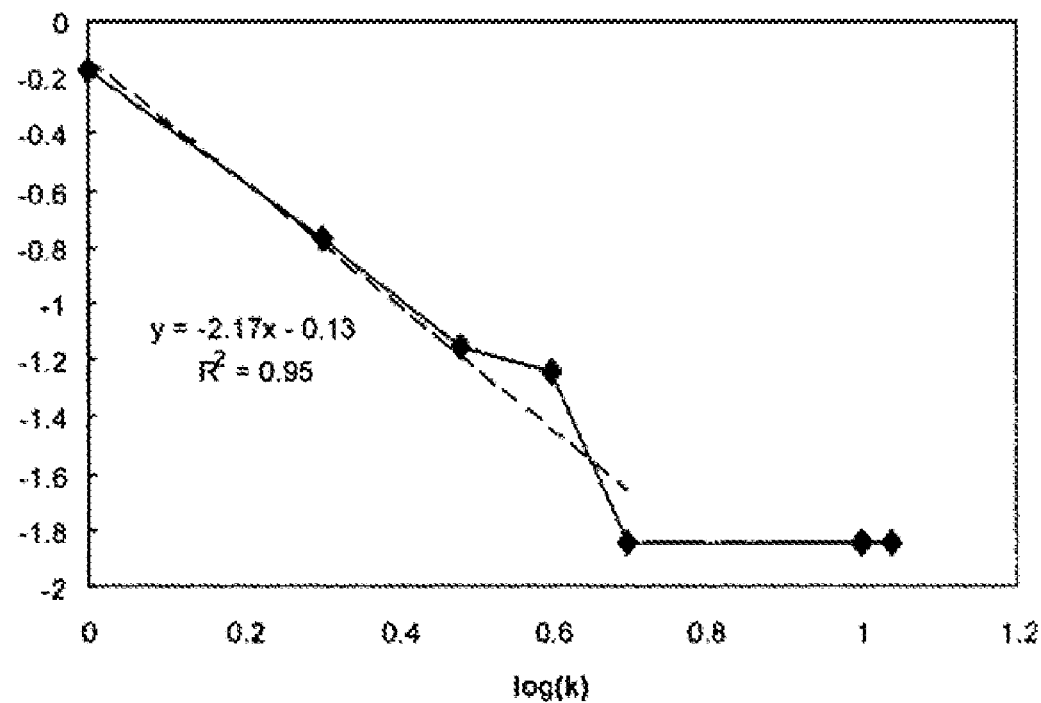

FIG. 5 is the log-log plot of k vs. P(k) of gene expression data for an arbitrarily chosen Downs and Control sample. The resulting plot is linear, demonstrating both modular and scale-free characteristics. The network organization appears to be hierarchical in nature for smaller clusters but deviates from linearity for larger clusters. This could be due to an effect called saturation that limits how large a cluster can get in real-world networks, due to physical constraints and stability.

Figure 6:
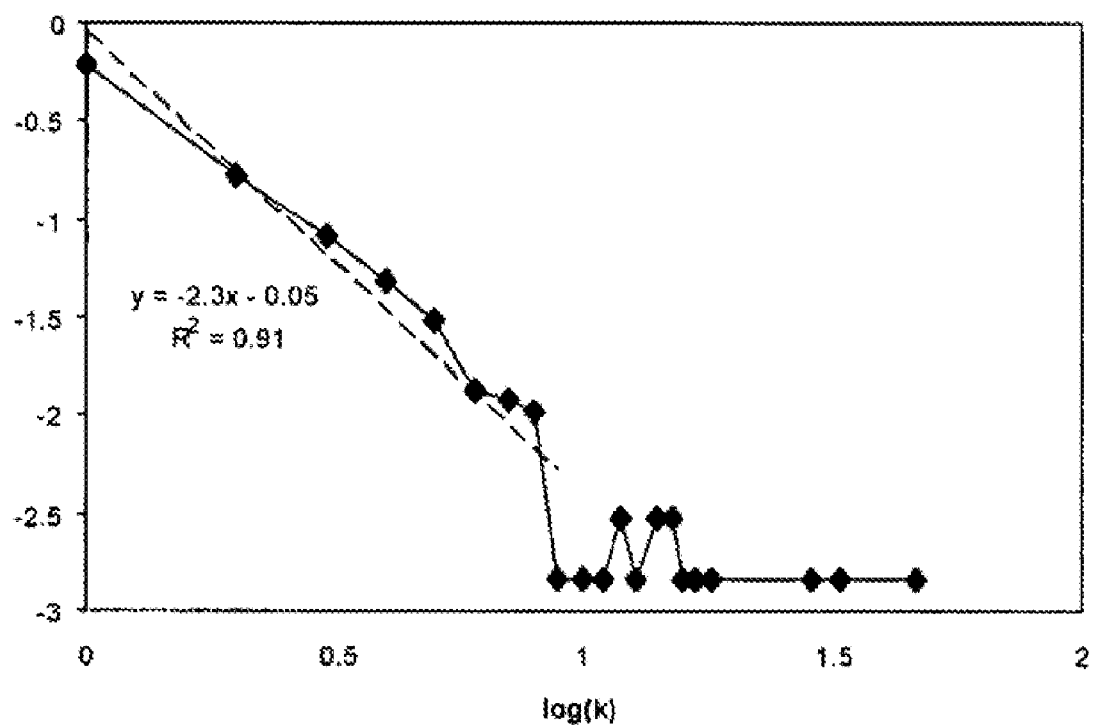
FIG. 6 is a log-log probability distribution for lined FGM models derived from all gene expression data of Control/Normal subject and Down's Syndrome subject in the study. Dashed line=scale-free fit.

FIG. 6 is the same plot derived from clusters for all samples on the same FGM map. This is, in effect, a picture of the combined genome for all the data. The picture conveyed from FIGS. 5 and 6 together brings to light further notions of universal constructs within such complex networks.

Using the method described above, a 7-gene group was discovered that corresponded only to subjects with Down's syndrome. The corresponding results are shown in Tables 1 and 2.

TABLE 1

Ranked absolute values of the Pearson Correlation for 7-gene FGM models with the 7-gene biomarker candidate model (left) and the corresponding correlations with actual expression values (right). Down's subject marked with "D" (The model/actual values of the genes from subject marked with * were used.)

| Subject | Pearson | Subject | Pearson |
| --- | --- | --- | --- |
| 6-194D* |  | 6-194D | 1 |
| 4213-34D | 1 | 42135-34D | 0.97 |
| 5-186D | 1 | 5-186D | 0.97 |
| 7-197D | 0.92 | 10-A01C | 0.89 |
| 8-367C | 0.87 | 7-197D | 0.88 |
| 10-A01C | 0.83 | 3648FC | 0.85 |
| 9-367C | 0.62 | 8-367C | 0.84 |
| 3648FC | No model found | 9-367C | 0.71 |

TABLE 2

The 7-gene Down's Syndrome biomarker candidate. Model and actual gene expression values for subject 6-194D (produced highest correlation in Table 1) and description of genes in the group. *Denotes the fact that this model is negatively correlated to the actual values (absolute Pearson used in model scoring).

| FGM (Model) Values* | Actual Values |
| --- | --- |
| 57.5 | 200.9 |
| 112.3 | 22.5 |
| 70.9 | 170.7 |
| 106.9 | 7.9 |
| 103.3 | 8.2 |
| 99.7 | 14.5 |
| 112.9 | 4.7 |

Cluster Incl. D11466: *Homo sapiens* mRNA for PIG-A protein
Cluster Incl. D10925: Human mRNA for HM145
Cluster Incl. U13395: Human oxidoreductase
Human scavenger receptor cysteine rich Sp alpha mRNA
*Homo sapiens* properdin (PFC) gene
*H. sapiens* mRNA for BMPR-II
Human apoptotic cysteine protease The 7-gene Downs biomarker candidate found was located within some of the larger clusters (which did not contain any control samples of the same gene group) on the FGM surface. This could be significant when exploring linkages to larger gene groups.

To test for artifacts from the FGM surface, a "random" U-95A mock sample, produced from 12,558 uniformly distributed random numbers from 0-10000, was analyzed as 7-gene groups. Only one cluster of three genes and 23 pair-clusters were found in the entire sample.

Example 2

Identification of Biomarkers in Human Immunodeficiency Virus (HIV) Infection

In this example, FGM was used to model small groups of 14 genes from much larger microarrays (Affymetrix Human Genome U95A chips) consisting of 12,558 genes. The data was derived from the brain tissue of 5 HIV-1 negative and 4 HIV-1 infected subjects—totaling 9 subjects. The number of genes within the groups, in this case 14, was decided using the criteria of picking a relatively small number—in the range of 5-20—that goes evenly into 12,558. Thus, arbitrarily choosing the gene groups by grouping the genes as they appeared on the gene chip, 897 14-gene groups were established. Consequently, 8,073 (897 gene groups*9 subjects) target strings, M, each with 14 gene expression values, were provided for FGM analysis.

Comparison strings were generated for each target string, as previously described. These FGM models were scored based on their overall Pearson correlation, using a minimum cutoff correlation of absolute value>0.95. Therefore, the overall magnitude of gene expression with in these small groups did not matter in probing for similar patterns throughout the array, only the relative expression patterns within the groups.

When comparing gene expression between the gene groups, the models of comparison strings were most often used, though sometimes the actual gene expression values were used.

Within the point-models on the FGM surface, clusters were found containing models of the same gene groups corresponding to only one of the phenotypes. One 14-gene group was discovered that corresponded only to HIV-1 infected subjects. This 14-gene group was then individually tested across all data for each subject in order to verify that between these n-gene patterns (n=14 in this case) the Pearson correlation was noticeably different depending on the phenotype from which the data sample was drawn. The 14-gene group from the sample within the cluster that produced the most noticeable difference was identified as a putative biomarker. The correlation values with this particular gene group and the corresponding gene groups, across all samples, are shown in Table 3. The left side of Table 3 uses the FGM model values, both ranked from highest to lowest correlation.

TABLE 3

Ranked absolute values of the Pearson Correlation for 14-gene
FGM models with the 14-gene biomarker candidate model (left)
and the corresponding correlations with actual expression values
(right). HIV-1 positive marked with "+". (The model/actual
values for the genes from subject marked with * were used.)

| Subject | Pearson | Subject | Pearson |
|---|---|---|---|
| G0036+* |  | G0036+* |  |
| G0017+ | 0.98 | D97 2916− | 0.97 |
| H0011+ | 0.94 | G0017+ | 0.96 |
| H0002+ | 0.91 | H0011+ | 0.94 |
| G0010+ | 0.86 | G0010+ | 0.92 |
| BTB 3455− | No model found | H0002+ | 0.89 |
| BTB 3648− | No model found | BTB 3648− | 0.88 |
| BTB 3749− | No model found | BTB 3455− | 0.72 |
| D97 2916− | No model found | BTB 3749− | 0.71 |

The actual marker genes and the model and actual expression values of the sample/subject that produced the greatest correlation are listed in Table 4.

TABLE 4

HIV-l brain biomarker candidate. Model and actual gene
expression values for subject G0036+ (produced highest
correlation in Table 3) and description of genes in the group.

| FGM (Model) Values | Actual Values |
|---|---|
| 310.8 | 180.7 |
| 126.3 | 55.6 |
| 298.8 | 158.4 |
| 264.5 | 51.9 |
| 274.4 | 174.7 |
| 585.9 | 912.1 |
| 233.4 | 264.3 |
| 248 | 245.6 |
| 478.6 | 572.3 |
| 144.4 | 55.2 |
| 363 | 218.5 |
| 328.3 | 312.4 |
| 457.5 | 626.5 |
| 1074 | 1593.2 |

Cluster Incl. U39067: *Homo sapiens* translation initiation factor eIF3 p36
Cluster Inc. AL050106: *Homo sapiens* mRNA; cDNA DKFZp586I1319
Cluster Incl. AF047181: *Homo sapiens* NADH-ubiquinone oxidoreductase
Cluster Incl. AF007872: *Homo sapiens* torsinB (DQ1)
Cluster Incl. AF007871: *Homo sapiens* torsinA
Cluster Incl. AB011116: *Homo sapiens* mRNA for KIAA0544
Cluster Incl. AF032456: *Homo sapiens* ubiquitin conjugating enzyme G2
Cluster Incl. D87454: Human mRNA for KIAA0265 gene
Cluster Incl. AF001383: *Homo sapiens* amphiphysin II mRNA
Cluster Incl. U69263: Human matrilin-2 precursor mRNA
Cluster Incl. D31889: Human mRNA for KIAA0072 gene
Cluster Incl. AL050265: *Homo sapiens* mRNA
Cluster Incl. AL038340: DKFZp566K192_s1
Cluster Incl. AL038340: DKFZp566K192_s1 (duplicate description)

Example 3

Genetic Network and Biomarkers in Leukemia

Input data from the study produced by Golub et al. (Golub T R., et al., *Science*, Vol. 286, pp. 531-536, 1999) are used in this example in order to further demonstrate the utility of the present invention. The data in the Golub study contained Affymetrix gene expression data for 7070 genes acquired from patients diagnosed with either acute lymphoblastic leukemia (ALL) or acute myeloid leukemia (AML). The data was composed of a training set of data from 27 ALL patients and 11 AML patients to develop diagnostic approaches based on the Affymetrix data and an independent set of 34 patients for testing.

Genetic Network in the Clinical Expression of Leukemia

In order to determine what kind of genetic network is involved in the clinical expression of leukemia, the more than 7000 gene expression values in the Golub data were broken into groupings of 5, 7, and 10 genes based only on the order in which the genes were arranged on the Affymetrix chip. FGM was used to create point-models of the gene expression patterns in these small groups and looked for correlations, or clustering between the 5, 7, and 10 gene models in each of the 38 patients in the Golub training set.

The number of ways to arrange to arrange 7 genes out of 7000 is ~$10^{27}$. Unless there is coordinated behavior between a large number of these 7000 genes, there would be almost no chance of finding correlations between (effectively) arbitrary 7-gene groupings, even when clustering a thousand of them. On the other hand, if there is a genetic network of the scale-free type described above, there should be a large number of genes whose behavior is correlated to only a few genes.

For the 7-gene grouping, our analysis found that there were significant model clusters in every patient. The largest cluster had an average size of approximately ten 7-genes models. Pearson correlations of >|0.95| between the models confirmed the similarities within these clusters. This provides statistical evidence that there are at least a few genes whose behavior is connected with well over 1000 other genes. This also agrees with an earlier gene expression study based on time-based gene expression data.

The clusters that contained 7-gene groups from only the patients with ALL were then scrutinized. Two 7-gene group models correlated to the largest number of corresponding models in ALL patients but with no AML patients. The two 7-gene groups are listed in Table 5 with their respective gene model values as well as the actual gene expression values.

TABLE 5

Gene Segments Used

| | Gene Model Values | Actual |
|---|---|---|
| 7-Gene Group 1 | | |
| GATA2 GATA-binding protein 2 | 572.9 | 635 |
| Alcohol dehydrogenase 6 gene | 771.8 | 346 |
| GB DEF = Protein-tyrosine phosphatase mRNA | 997.4 | 442 |
| Globin gene | 1310.9 | 362 |
| Pre-mRNA splicing factor SF2, P32 subunit precursor | 1848.7 | 859 |
| Major histocompatibility complex enhancer-binding protein MAD3 | 3047.3 | 2281 |
| MSN Moesin | 6975 | 6975 |
| 7-Gene Group 2 | | |
| Onconeural ventral antigen-1 (Nova-1) mRNA | 828.7 | 93 |
| Ini1 mRNA | 758.9 | 123 |
| RORA RAR-related orphan receptor A | 237 | −60 |
| FUSE binding protein mRNA | 1345.7 | 891 |
| Rar protein mRNA | 958.5 | −38 |
| Fetal Alz-50-reactive clone 1 (FAC1) mRNA | 1616.6 | 635 |
| MB-1 gene | 5244 | 5314 |

These two 7-gene group models were used for a 7-gene diagnostic test. The two 7-gene group model values from two patients in the training set (above) were used to characterize ALL in the independent set. The test was an OR test, where if either of the corresponding 7-gene models in the independent set patients had a Pearson correlation with these 7-gene model values such that the absolute value was >0.95, the patient was classified as ALL. The results for the 7-gene grouping are as follows:

| | |
|---|---|
| Overall Accuracy | 0.853 |
| ALL only | 0.95 |
| AML only | 0.714 |

Pathways related to this result comprise the Ras-Independent pathway in NK cell-mediated toxicity. The gene of special interest from this result is MB-1 gene.

In addition, it was found that the second 7-gene group above allows for the differentiation of patients with ALL into those who have the T-cell ALL from B-cell ALL. The test using this 7-gene group model was accurate to 100% in the test set in classifying B-cell vs. T-Cell(See Table 6). The gene segments used are summarized in Table 7.

TABLE 6

Summary of using the second 7-gene group to predict B-cell and T-cell ALL

| Gene-chip (Patient) | Absolute Pearson correlation between patient gene segment model and classifier model | Predicted (> .95 = B-Cell) | Actual | Correct |
|---|---|---|---|---|
| 39 | 0.9997 | B-Cell | B-Cell | Yes |
| 40 | 0.9509 | B-Cell | B-Cell | Yes |
| 41 | 0.9954 | B-Cell | B-Cell | Yes |
| 42 | 1 | B-Cell | B-Cell | Yes |
| 43 | 0.9974 | B-Cell | B-Cell | Yes |
| 44 | 0.9995 | B-Cell | B-Cell | Yes |
| 45 | 1 | B-Cell | B-Cell | Yes |
| 46 | 0.9995 | B-Cell | B-Cell | Yes |
| 47 | 0.9996 | B-Cell | B-Cell | Yes |
| 48 | 0.9999 | B-Cell | B-Cell | Yes |
| 49 | 0.9999 | B-Cell | B-Cell | Yes |
| 55 | 0.9792 | B-Cell | B-Cell | Yes |
| 56 | 1 | B-Cell | B-Cell | Yes |
| 59 | 0.9616 | B-Cell | B-Cell | Yes |
| 67 | 0.6753 | T-Cell | T-Cell | Yes |
| 68 | 1 | B-Cell | B-Cell | Yes |
| 69 | 0.9996 | B-Cell | B-Cell | Yes |
| 70 | 0.9998 | B-Cell | B-Cell | Yes |
| 71 | 1 | B-Cell | B-Cell | Yes |
| 72 | 0.9998 | B-Cell | B-Cell | Yes |

TABLE 7

Gene Segments Used to predict B-cell and T-cell ALL

| Gene Segment (Classifer) | Used | Gene Model (Classifier) Values | Actual Values |
|---|---|---|---|
| Onconeural ventral antigen-1 (Nova-1) mRNA | U04840_at | 828.711548 | 93 |
| Ini1 mRNA | U04847_at | 758.938538 | 123 |
| RORA RAR-related orphan receptor A | U04898_at | 237.028641 | −60 |
| FUSE binding protein mRNA | U05040_at | 1345.72998 | 891 |
| Rar protein mRNA | U05227_at | 958.517456 | −38 |
| Fetal Alz-50-reactive clone 1 (FAC1) mRNA | U05237_at | 1616.58411 | 635 |
| MB-1 gene | U05259_rna1_at | 5244.02344 | 5314 |

Clusters were also found in the 5 and 10 gene grouping runs. These clusters were generally smaller but the analysis of these groups also gave indications of large-scale correlation between many genes. The five gene-grouping runs resulted in several 5-gene groups. Table 8a lists gene group models used for 5-gene diagnostic tests. Five different gene model value sets consisting of four 5-gene groups each (20 genes total) were used to create five different 5-gene diagnostic tests. The results are provided in Table 8b.

TABLE 8a

| | Gene Model Values | Actual |
|---|---|---|
| Gene group used in every 5-gene diagnostic test | | |
| Serine/Threonine protein phosphatase 2B catalytic subunit, beta isoform | 653.5 | 287 |
| Serine/Threonine protein phosphatase 2B catalytic subunit, beta isoform | 885.9 | 190 |
| ZNF7 Zinc finger protein 7 (KOX 4, clone HF.16) | 179.4 | −284 |
| ZNF8 Zinc finger protein 8 (clone HF.18) | 1263.7 | 739 |
| IL7R Interleukin 7 receptor | 3862.7 | 3863 |
| Gene group used in every 5-gene diagnostic test | | |
| MCMB Minichromosome maintenance deficient (S. cerevisiae) 3 | 1654.2 | 1848 |
| TBXA2R Thromboxane A2 receptor | 1308.5 | 1534 |
| GB DEF = Fas ligand (FasL) mRNA | 320.8 | 188 |
| COL19A1 Collagen, type XIX, alpha 1 | −128.5 | −372 |
| DNA-DIRECTED RNA POLYMERASE II 23 KD POLYPEPTIDE | 830.5 | 820 |
| Gene group used in 5-gene diagnostic test #2, #4 and #5 | | |
| DNA for rhoHP1 | 305.4 | 167 |
| P97 homologous protein | 94.7 | 2 |
| EP3-IV gene extracted from Human DNA for prostaglandin E receptor EP3 subtype | 143.3 | 14 |
| Osteoblast mRNA for osteonidogen | 142.9 | 22 |
| Non-lens beta gamma-crystallin like protein (AIM1) mRNA partial cds | 513.9 | 514 |
| Gene group used in 5-gene diagnostic test #1, #3 and #4 | | |
| Na, K-ATPase subunit alpha 2 (ATP1A2) gene | 33.2 | 50 |
| PNL1P Pancreatic lipase | 118.8 | −57 |
| CARBOXYPEPTIDASE N 83 KD CHAIN | −46.6 | −172 |
| GB DEF = Sialoprotein mRNA | 62.8 | −86 |
| SPTAN1 Spectrin, alpha, non-erythrocytic 1 (alpha-fodrin) | 661 | 661 |
| Gene group used in 5-gene diagnostic test #3 and #5 | | |
| PLA2G4 Phospholipase A2, group IV | −31.7 | −45 |
| GATA2 GATA-binding protein 2 | −38.1 | 635 |
| Alcohol dehydrogenase 6 gene | −35.3 | 346 |
| GB DEF = Protein-tyrosine phosphatase mRNA | −36.6 | 442 |
| Globin gene | −36 | 362 |
| Gene group used in 5-gene diagnostic test #1 only | | |
| Proton-ATPase-like protein | 365.2 | 216 |
| Sro-like adapter protein mRNA | 115.6 | 67 |
| N-Acetyl-beta-D-glucosaminide | 484.8 | 184 |
| PBI gene | 357.9 | 41 |
| C-myc binding protein | 1269.5 | 1271 |
| Gene group used in 5-gene diagnostic test #2 only | | |
| KIAA0250 gene | 1012 | 1269 |
| KIAA0251 gene, partial cds | 596.3 | 870 |
| K1AA0252 gene, partial cds | −265.5 | −177 |
| K1AA0253 gene, partial cds | 613.6 | 1088 |
| K1AA0254 gene | −246.3 | −383 |

TABLE 8b

| Results from 5-gene test 1: | |
|---|---|
| Overall Accuracy | 0.824 |
| ALL only | 0.8 |
| AML only | 0.857 |
| Results from 5-gene test 2: | |
| Overall Accuracy | 0.735 |
| ALL only | 0.8 |
| AML only | 0.643 |
| Results from 5-gene test 3: | |
| Overall Accuracy | 0.824 |
| ALL only | 0.8 |
| AML only | 0.857 |
| Results from 5-gene test 4: | |
| Overall Accuracy | 0.765 |
| ALL only | 0.8 |
| AML only | 0.714 |
| Results from 5-gene test 5: | |
| Overall Accuracy | 0.735 |
| ALL only | 0.75 |
| AML only | 0.714 |

Pathways related to this result comprise:
Regulation of hematopoiesis by cytokines,
IL-2 Receptor Beta Chain in T cell Activation,
Tumor Supporessor Arf Inhibits Ribosomal Biogenesis,
Neuropeptides VIP and PACAP inhibit the apoptosis of activated T cells,
FAS signaling pathway ( CD95 ),
HIV-I Nef: negative effector of Fas and TNF,
Fc Epsilon Receptor I Signaling in Mast Cell,
p38 MAPK Signaling Pathway, and
Induction of apoptosis through DR3 and DR4/5 Death Receptors.

Table 9a lists gene group models used for 10-gene diagnostic tests. Two different gene model values sets consisting of two 10-gene groups each (50 genes total) were used to create two different 10-gene diagnostic tests. The results are provided in Table 9b.

TABLE 9a

|  | Gene Model Values | Actual |
|---|---|---|
| Gene group 1 | | |
| RBQ-3 mRNA | 108.6 | 142 |
| SURF-5 mRNA | −73.4 | −119 |
| Splicing factor SF3a120 | 119.7 | 186 |
| Sm protein F | 831.1 | 1785 |
| Sm protein G | 656 | 1195 |
| GB DEF = Protein kinase PKX1 | 221.6 | 399 |
| C-C chemokine receptor-4 | −291.9 | −347 |
| Transcript associated with monocyte to macrophage differentiation | 127.5 | 26 |
| Cell division protein kinase 8 | 89.1 | 57 |
| DARC gene | 179.1 | 433 |
| Gene group 2 | | |
| Spliceosome associated protein (SAP 145) mRNA | −344.4 | 1200 |
| Gu protein mRNA, partial cds | −69 | 199 |
| Deleted in split hand/split tool 1 (DSS1) mRNA | 42.5 | 336 |
| OS-9 precurosor mRNA | −457.3 | 1696 |
| DGUOK Deoxyguanosine kinase | −163.9 | 428 |
| GB DEF = Pancreatic beta cell growth factor (INGAP) mRNA | 210.3 | 8 |
| PDGF associated protein mRNA | 223.9 | 48 |
| CLTC Clathrin heavy chain (alternative products) | 309.9 | −485 |
| Putative T1/ST2 receptor binding protein precursor mRNA | 362.6 | −581 |
| HOXA9 Homeo box A9 | 149.3 | 24 |
| Gene group 3 | | |
| SOD1 Superoxide dismutase 1 (Cu/Zn) | −201.2 | 2925 |
| CALCB Calcitonin-related polypeptide, beta | −197.6 | 49 |
| INP10 Interferon (gamma)-induced cell line, protein 10 from ORM1 Orosomucoid 1 | −197.7 | −217 |
| GB DEF = Bcr (breakpoint cluster region) gene in Philadelphia chromosome | −197.9 | 745 |
| CYP1A1 Cytochrome P450, subfamily 1 (aromatic compound-inducible), polypeptide 1 | −197.9 | 27 |
| PROC Protein C (inactivator of coagulation factors Va and VIIIa) | −197.9 | 509 |
| NRAS Neuroblasioma RAS viral (v-ras) oncogene homolog | −197.9 | 117 |
| OIAS (2'-5') oligoadenylate synthetase | 197.9 | 97 |
| TNF Tumor necrosis factor | −197.9 | 237 |
| Gene group 4 | | |
| GB DEF = Propionyl-CoA carboxylase beta-subunit (beta-PCC) gene, partial cds (mutant d | 199.9 | 258 |
| MYL1 Myosin light chain (alkali) | 99.7 | 547 |
| GB DEF = Complement receptor 1 (CR1) gene, exon 4 | 109.7 | 44 |
| TCF3 Transcription factor 3 (E2A immunoglobulin enhancer binding factors E 12/E47) | 603.5 | 1555 |
| GB DEF = (clone lambda-16-1) non-receptor tyrosine phosphalase 1 (PTPN1) gene, exon | 172.1 | 699 |
| Proto-oncogene BCL3 gene | 565 | 1653 |
| TSHR Thyroid stimulating hormone receptor | 106.4 | 348 |
| GB DEF = Fc-gamma-R11A gene for fgG Fc receptor class 11A (5'flank) | −92.2 | −139 |
| HIVEP1 Human immunodeficiency virus type 1 enhancer-binding protein 1 | 146.6 | 383 |
| Phosphoribosylamine-glycine ligase | 14.4 | −23 |
| Gene group 5 used only in test #1 | | |
| CLTB clathrin, light polypeptide (Lcb) | 453 | −95 |
| GB DEF = G-protein coupled receptor | 874.5 | 662 |
| GLUL Glutamate-ammonia ligase (glutamine synthase) | −41.6 | −7 |
| ZNF183 gene | 669.1 | 1015 |
| GB DEF = Bone marrow serine protease gene (medullasin) (leukocyte neutrophil elastase | 1318.4 | 790 |
| N-Oct 3, N-Oct5a, and N-Oct 5b proteins | 331 | −173 |
| Alpha-Centractin | 1009.5 | 554 |
| Red-Sensitive Opsin | 434.3 | −60 |
| GB DEF = DNA sequence from PAC 151B14 on chromosome 22q12-qter contains somato | 1063.8 | 882 |
| GB DEF = Immunoglobulin-related 14.1 protein mRNA | 3777.4 | 3807 |
| Gene group 5 used only in test #2 | | |
| SIAT1 Sialyltransferase 1 (beta-galactoside alpha-2,6-sialyltransferase) | 512.8 | 815 |
| RHD Rhesus blood group, D antigen | 989.2 | 1793 |
| HE4 mRNA for extracellular proteinase inhibitor homologue | 761.2 | 879 |
| GB DEF = HB2A gene for high sulfur keratin | 166.9 | 188 |
| Udp-Glucuronosyl Transferase 2b10 Precursor, Microsomal | 283.6 | 70 |
| Myocyte-Specific Enhancer Factor 2 | 173.4 | 22 |
| GB DEF = 1rIB mRNA | 146.4 | −39 |
| ATP5D ATP synthase, H+ transporting, mitochondrial F1 complex, delta subunit | 480.4 | 926 |
| GB DEF = Hst-2 (FGF-6) mRNA | 203.8 | 12 |
| GTF2E2 General transcription factor TFIIE beta subunit, 34 kD | 427.6 | 532 |

| Results from 10-gene test 1 | |
|---|---|
| Overall Accuracy | 0.735 |
| ALL only | 0.65 |
| AML only | 0.857 |
| Results from 10-gene test 2 | |
| Overall Accuracy | 0.676 |
| ALL only | 0.55 |
| AML only | 0.857 |

Pathways related to this result comprise
Free Radical Induced Apoptosis,
PDGF Signaling Pathway,
Rac 1 cell motility signaling pathway, and
Selective expression of chemokine receptors during T-cell polarization.

Genes of special interest from this result are SOD1, Sm protein F, Sm protein G, and HOXA9.

Transmission Pattern within the Network of ALL

In order to determine if a particular transmission pattern within this network (gene expression pattern) can be identified with acute lymphoblastic leukemia (ALL), point models from all 7-gene groups for all 38 patients were clustered. Clusters were examined that contained only 7-gene groups from the patients with ALL. Two 7-gene group model patterns, were identified which correlated with the largest number of corresponding models in other ALL patients and with none of the AML patients. To test how accurately these two patterns classified ALL patients, correlations were also tested this diagnostic/classification method on the Golub independent data. This method identified ALL patients form AML patients to ~85% accuracy. (See the Results section) This gives credence to this method both as a diagnostic technique and lends significance to the gene models used. The chance of these two gene group model patterns producing an 85% result by chance is roughly 1 in 50000. Similarly tests were performed on the 5 and 10 gene groups. The diagnostic accuracy varied from 67.6 to 82.4%. Many pathways and genes were identified as being significant in the course of this test. Several of these appeared to mesh with current knowledge in the field (See Results section).

The test cited above identified a particular group of genes and a gene expression pattern within them that appears to identify ALL. This does not necessarily mean, however, that this group of genes is in the hypothetical ALL ring within a network of the kind illustrated in FIG. 2. To produce evidence of this type of large-scale transmission a test was produced which compared all 7-gene models to all corresponding models between patients in the independent set and a randomly chosen ALL and AML patient from the training set. All model correlations were calculated and averaged for both the ALL and AML patients chosen. The diagnostic decision was based on which comparison had the higher average correlation. This test produced a diagnostic accuracy of 82.4%. More importantly, this result is a statistically significant indication of gene expression pattern reflecting a clinical expression of ALL throughout the 7000+ gene set. The same test was also performed with the 10-gene models to also produce a statistically significant result (See Results section).

The results of the 7-gene grouping all models to all models diagnostic test (based on average correlation with randomly chosen ALL and AML patient from the training set) are as follows:

| Overall Accuracy | 0.824 |
|---|---|
| ALL only | 0.85 |
| AML only | 0.786 |

The results of the 10-gene grouping all models to all models diagnostic test (based on average correlation with randomly chosen ALL and AML patient from the training set) are as follows:

| Overall Accuracy | 0.735 |
|---|---|
| ALL only | 0.7 |
| AML only | 0.786 |

The results for all 7-gene models to 7-gene group1 model pattern diagnostic test (based on average correlation with randomly chosen ALL and AML patient from the training set) are as follows:

| Overall Accuracy | 0.765 |
|---|---|
| ALL only | 0.9 |
| AML only | 0.571 |

Upstream and Downstream Pathways in ALL Genetic Network

It can be further determined if this transmission pattern be traced upstream in the network. Starting with the two specific 7-gene model patterns used to diagnosis ALL, an attempt was made to find correlations between these patterns and all 7-gene models in both ALL and AML patients in the training set.

The assumption was that finding this expression pattern in an area closer inside than the "ALL ring" in FIG. 4 would constitute finding an upstream gene grouping. In this area ALL and AML have yet to reach genes which will determine their specific clinical expression.

There was one 7-gene grouping whose models correlated with one of the ALL diagnostic patterns in all patients, both ALL and AML. There were also two other 7-gene groups that met this condition in almost all patients in the training set. All three of the gene groups are listed under the heading "Most Common Upstream Gene Groups correlated to 7-gene Model Patterns Used in Diagnostic Test" in the Results section.

To strengthen the assumption that this pattern was being transmitted through a large section of the network, we performed the following test. We correlated the single 7-gene diagnostic pattern cited above against all the 7-gene models in each of the AML patients in the training set. The highest average correlation was found. The same correlation test was performed across all the independent patients. A patient was identified as ALL if the average correlation was greater than the highest average AML correlation from the training set. This test identified ALL to ~76% accuracy. The diagnostic score is somewhat low, but the probably of chance occurrence is roughly 1 in a 1000. This provides statistical evidence that not only can large-scale gene expression be seen in ALL patients, a single pattern can be seen as being transmitted through a large section of a genetic network involved in the clinical expression of ALL.

Most common upstream gene Groups correlated to 7-gene model patterns which can be used in a diagnostic test are:

Group 1
  GAA gene extracted from Human lysosomal alpha-glucosidase gene exon 1
  AGA Aspartylglucosaminidase
  2-19 gene (2-19 protein) extracted from *H. sapiens* G6PD gene for glucose-6-phosphate dehydrogenase
  CYCLIC-AMP-DEPENDENT TRANSCRIPTION FACTOR ATF-1
  Usf mRNA for late upstream transcription factor
  PRTN3 Proteinase 3 (serine proteinase, neutrophil, Wegener granulomatosis autoantigen)
  RPS3 Ribosomal protein S3
Group 2
  XP-C repair complementing protein (p58/HHR23B)
  KIAA0031 gene
  Estrogen responsive finger protein
  C3G protein
  CDH11 Cadherin 11 (OB-cadherin)
  60S RIBOSOMAL PROTEIN L23
  SM22-ALPHA HOMOLOG
Group 3
  CD1D CD1D antigen, d polypeptide
  5,10-methenyltetrahydrofolate synthetase mRNA
  PTPRD Protein tyrosine phosphatase, receptor type, delta polypeptide
  GT197 partial ORF mRNA, 3' end of cds
  The longest open reading frame predicts a protein of 202 amino acids, with fair Kozak consensus at the initial ATG codon; an in-frame TGA codon is seen at nucleotide 8; ORF; putative gene extracted from *Homo sapiens*
  GT198 mRNA, complete ORF
  GT212 mRNA
  RPL37 Ribosomal protein L37
Pathways related to upstream gene groups comprise:
  Oxidative reactions of the pentose phosphate pathway,
  TNF/Stress Related Signaling, fMLP induced chemokine gene expression in HMC-1 cells,
  Proepithelin Conversion to Epithelin and Wound Repair Control,
  Rac 1 cell motility signaling pathway, and
  Catabolic pathway for asparagine and asparate.

Figure 7:
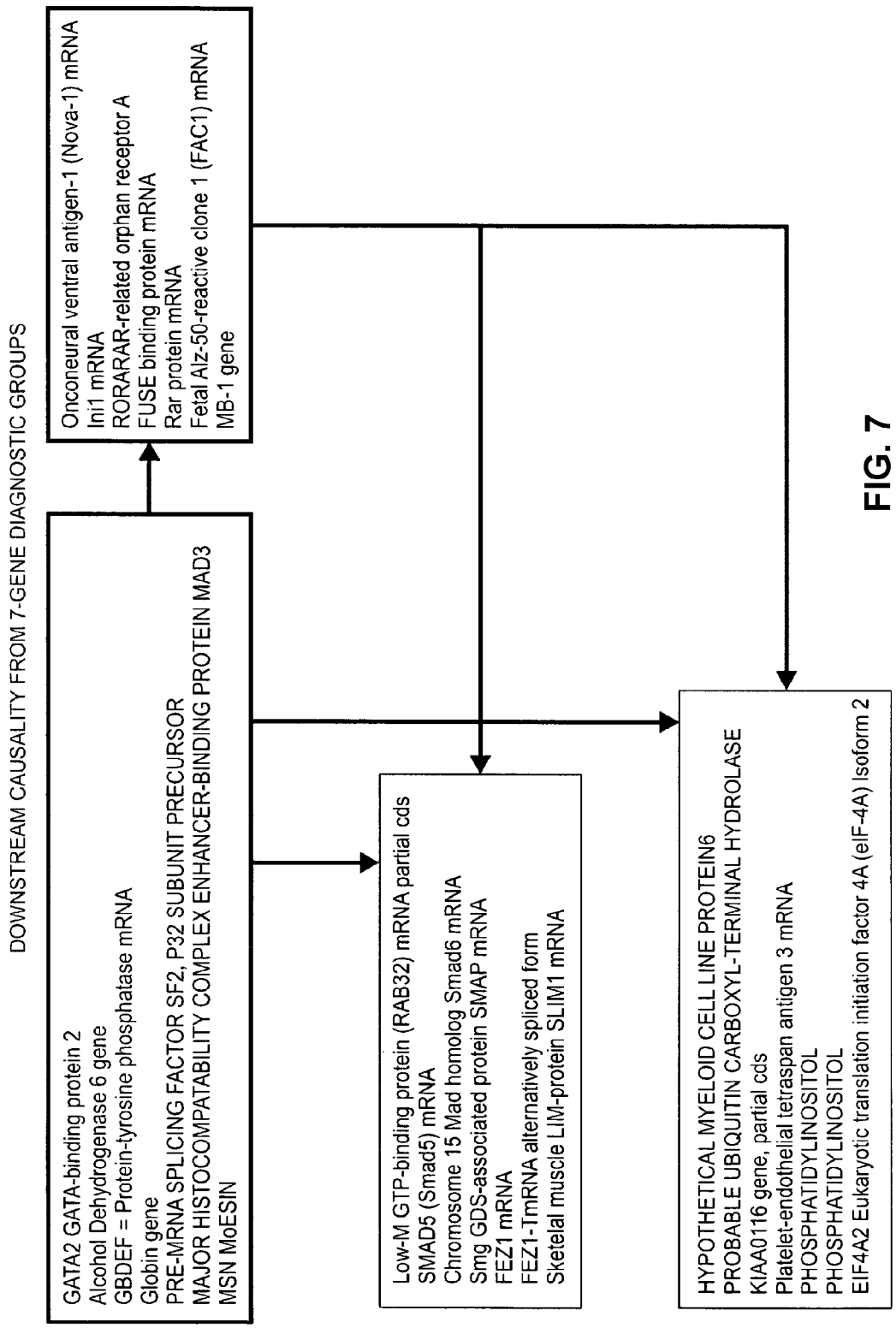
FIG. 7 is a flow chart showing a downstream causality from two diagnostic 7-gene groups used in the 7-gene test in Example 3.

FIG. 7 shows a preliminary diagram of downstream causality from two diagnostic 7-gene groups used in the 7-gene test. Pathways related to downstream causality groups comprise ALK in cardiac myocytes, WNT Signaling Pathway, BCR Signaling Pathway, Fc Epsilon Receptor I Signaling in Mast Cell, Neuropeptides VIP and PACAP inhibit the apoptosis of activated T cells, Regulation of hematopoiesis by cytokines, Cytokines and Inflammatory Response, Integrin Signaling Pathway, AKT Signaling Pathway, Regulation of transcriptional activity by PML, mTOR Signaling Pathway, and Regulation of eIF4e and p70 S6 Kinase.

Genes of special interest from this result include: FEZ1, EIF4A

Causal Picture of the Network

In order to determine if a transmission pattern can be used to create a causal picture of the network, a partial picture of causality going downstream from the 7-gene diagnostic groups was constructed using a combination of correlations with the actual diagnostic patterns and correlations with the actual 7-gene diagnostic group models for each patient. A 7-gene group was considered a candidate for a downstream link if the gene model did not correlate with the corresponding model in any of the ALL patients, and its 7-gene model correlated with one of the two diagnostic patterns. Downstream causality was considered found when the last condition only occurred when there was a correlation between its 7-gene model and the diagnostic group 7-gene models. The assumption is that this 7-gene group's expression (as part of an ALL network) was apparently "switched on" by the diagnostic 7-gene group correlation upstream. The results of this preliminary causal analysis are in the Results section.

In summary, this example describes a method of pathway conjecture and diagnosis using fractal genomics modeling (FGM). The 7-gene group results were focused on but many interesting pathway and gene inferences seems to come out of the 5 and 10 gene tests. Within the related pathways listed there is a great deal of overlap between the pathways connected with the downstream links and the 5-gene groups. This is intriguing because in a scale-free network of the kind shown in FIG. 2, the genes with 5 links would tend to be both downstream of genes with 7-links and also more prevalent. This could provide a framework for building the interconnected downstream pathways actually represented in these groups. This would also lend credence to the idea that the 10-gene models tend to reflect pathways upstream of the 7-gene groups. Together these two notions could perhaps be used to map the biochemistry within the "ALL ring" in FIG. 4. This also might explain why the 5-gene and 10-gene results were results less accurate, since they were dealing with pathways slightly removed from the "critical point" in ALL clinical expression. There could also be other biophysical reasons for this. Statistical evidence was produced toward validation of the model of clinical expression shown in the genetic network in FIG. 4. In this process of arriving at this evidence new tools and approaches have been identified for extracting a great deal of information about the structure and function of such a network. New diagnostic methods have also been identified. The diagnostic results, although statistically significant, were still somewhat low compared to other methods. This could well be due to problems with the Golub methodology which were accurately portrayed in a false diagnosis by FGM. We will apply FGM to more up-to-date and accurate gene expression studies to further validate, improve, and extend the diagnostic approaches and pathway information of this invention. In the process we will continue to translate the biophysics of gene expression models into the pathways and targets of interest to researchers in the medical field. Since FGM is data independent, we hope to apply these approaches to proteomic and even clinical data as well.

While specific embodiments have been illustrated and described, numerous modifications come to mind without departing from the spirit of the invention and the scope of protection is only limited by the scope of the accompanying claims.

What is claimed is:

1. A computerized method for visualizing patterns within a plurality of datasets, the method comprising:
  (a) inputting the plurality of datasets into a computer;
  (b) defining a first dataset of the plurality of datasets comprising a target string comprising a numerical sequence;
  (c) defining a region comprising a plurality of points, wherein each point serves as a domain of an iterative algorithm for generating a comparison string, and wherein the region is selected from the group consisting of a Mandelbrot set and a Julia set;
  (d) selecting a point in the region;
  (e) generating a comparison string comprising a second dataset from the selected point using the iterative algorithm;
  (f) scoring the comparison string to generate a score by testing the comparison string against the target string;
  (g) determining if the score meets a pre-determined condition;

(h) marking the point within the region if the score meets the pre-determined condition to represent a point-model of the first dataset in a human readable format; and (i) generating a visual display wherein the point is graphically displayed at coordinates within a grid that corresponds to the region, and wherein a location of the point within the region is an indicator of similarity of the first dataset to other datasets of the plurality of datasets.

2. The method of claim 1, wherein the steps (d) through (h) are repeated for a plurality of target strings corresponding to one or more other datasets of the plurality to generate a plurality of point-models in the region to form a map of the point-models.

3. The method of claim 1, wherein the step of selecting a point comprises selecting the point within the grid of the visual display.

4. The method of claim 1, wherein the dataset of the comparison string is of any length.

5. The method of claim 1, wherein the step of generating the comparison string further comprises selecting a new point for iteration if the iteration from the point becomes unbounded.

6. The method of claim 1, wherein scoring comprises a one-to-one comparison between the corresponding data in the target string and in the comparison string.

7. The method of claim 6, wherein the one-to-one comparison is between corresponding sequential or non-sequential data in the target string and in the comparison string.

8. The method of claim 1, wherein scoring of the comparison and target strings is based on Pearson Correlation between the strings.

9. The method of claim 1, wherein marking comprises storing the coordinates of the point corresponding to the target string or properties of the comparison string in memory, a database, or a table.

10. The method of claim 1, wherein the point is displayed by changing color of a pixel in the grid.

11. The method of claim 1, wherein the point-model functions as data compression for the target string.

* * * * *